(12) United States Patent
Suzuki

(10) Patent No.: US 8,748,692 B2
(45) Date of Patent: Jun. 10, 2014

(54) ABSORBENT ARTICLE AND SURFACE SHEET THEREOF

(75) Inventor: Rie Suzuki, Sakura (JP)

(73) Assignee: Daio Paper Corporation, Ehime (JP)

( * ) Notice: Subject to any disclaimer, the term of this patent is extended or adjusted under 35 U.S.C. 154(b) by 1289 days.

(21) Appl. No.: 11/887,520

(22) PCT Filed: Mar. 27, 2006

(86) PCT No.: PCT/JP2006/306088
§ 371 (c)(1),
(2), (4) Date: Sep. 27, 2007

(87) PCT Pub. No.: WO2006/104074
PCT Pub. Date: Oct. 5, 2006

(65) Prior Publication Data
US 2009/0137976 A1    May 28, 2009

(30) Foreign Application Priority Data

Mar. 29, 2005   (JP) ................................. 2005-094501

(51) Int. Cl.
*A61F 13/512* (2006.01)
*A61F 13/511* (2006.01)

(52) U.S. Cl.
USPC .......................................... 604/380; 604/383

(58) Field of Classification Search
USPC ............ 646/369; 428/137; 604/369, 367, 383
See application file for complete search history.

(56) References Cited

U.S. PATENT DOCUMENTS

| | | | | |
|---|---|---|---|---|
| 3,046,986 A | * | 7/1962 | Harwood ...................... | 604/375 |
| 3,575,764 A | * | 4/1971 | McFarren ................... | 156/306.6 |
| 3,718,537 A | * | 2/1973 | Kawai et al. ................. | 62/157.7 |
| 4,151,240 A | * | 4/1979 | Lucas et al. .................... | 264/504 |
| 4,280,978 A | * | 7/1981 | Dannheim et al. ............ | 264/156 |
| 4,323,068 A | * | 4/1982 | Aziz .............................. | 604/370 |
| 4,379,192 A | * | 4/1983 | Wahlquist et al. ............ | 428/156 |
| 4,542,060 A | | 9/1985 | Yoshida et al. | |
| 4,591,523 A | * | 5/1986 | Thompson .................... | 428/131 |
| 4,726,976 A | * | 2/1988 | Karami et al. ................ | 428/137 |
| 4,780,352 A | * | 10/1988 | Palumbo ....................... | 428/138 |
| 5,229,186 A | * | 7/1993 | Tribble et al. ................ | 428/156 |
| 5,229,191 A | * | 7/1993 | Austin .......................... | 428/198 |
| 5,522,811 A | * | 6/1996 | Igaue et al. ................... | 604/378 |
| 5,613,960 A | | 3/1997 | Mizutani | |
| 5,628,738 A | * | 5/1997 | Suekane .................. | 604/385.26 |

(Continued)

FOREIGN PATENT DOCUMENTS

| | | |
|---|---|---|
| JP | 59-223350 | 12/1984 |
| JP | 3-123552 | 5/1991 |

(Continued)

*Primary Examiner* — Susan Su
(74) *Attorney, Agent, or Firm* — Jordan and Hamburg LLP

(57) ABSTRACT

Disclosed is an absorbent article having an absorbent member positioned between a liquid-permeable multilayer surface sheet and a backside sheet. A plastic film layer is laminated on the non-skin contact surface side of the multilayer surface sheet. The multilayer surface sheet has embossments in the form of a large number of elevated portions protruding outward, the elevated portions being formed by heating the sheet to a temperature higher than the melting point of the plastic film layer but lower than the melting point of the nonwoven fabric layer. The multilayer surface sheet is also provided with a large number of openings. The absorbent article has a highly spatial appearance, provides good cushioning effect with minimized skin contact, and retains uneven emboss, even upon absorption of a body fluid.

18 Claims, 5 Drawing Sheets

(56) References Cited

U.S. PATENT DOCUMENTS

| | | | |
|---|---|---|---|
| 5,702,571 A * | 12/1997 | Kamps et al. | 162/117 |
| 5,830,555 A * | 11/1998 | Srinivasan et al. | 428/137 |
| 5,968,031 A * | 10/1999 | Schmitz | 604/391 |
| 6,080,276 A * | 6/2000 | Burgess | 162/117 |
| 6,344,102 B1 * | 2/2002 | Wagner | 156/229 |
| 6,455,201 B1 * | 9/2002 | Sugikawa | 429/242 |
| 6,974,514 B2 * | 12/2005 | Hamulski et al. | 156/73.1 |
| 7,132,585 B2 * | 11/2006 | Kudo et al. | 604/380 |
| 7,220,332 B2 * | 5/2007 | Curro et al. | 156/229 |
| 7,258,910 B2 * | 8/2007 | Toyoshima et al. | 428/181 |
| 7,423,003 B2 * | 9/2008 | Volpenhein et al. | 510/438 |
| 7,803,244 B2 * | 9/2010 | Siqueira et al. | 156/229 |
| 8,361,913 B2 * | 1/2013 | Siqueira et al. | 442/394 |
| 2002/0099347 A1 * | 7/2002 | Chen et al. | 604/369 |
| 2003/0004481 A1 | 1/2003 | Matsuoka et al. | |
| 2004/0059310 A1 * | 3/2004 | Gagliardi et al. | 604/385.01 |
| 2004/0254556 A1 * | 12/2004 | Brisebois et al. | 604/385.01 |
| 2005/0027270 A1 * | 2/2005 | Cree et al. | 604/383 |
| 2005/0124957 A1 * | 6/2005 | Giloh | 604/385.03 |
| 2006/0128247 A1 * | 6/2006 | Skoog et al. | 442/384 |
| 2009/0123707 A1 * | 5/2009 | Skoog et al. | 428/172 |

FOREIGN PATENT DOCUMENTS

| | | |
|---|---|---|
| JP | 3-241052 | 10/1991 |
| JP | 7-328060 | 12/1995 |
| JP | 8-302555 | 11/1996 |
| JP | 9-507408 | 7/1997 |
| JP | 10-000112 | 5/1998 |
| JP | 2002-160293 | 6/2002 |
| JP | 2003-126147 | 5/2003 |
| JP | 2005-097782 | 4/2005 |
| WO | WO-03/048436 | 6/2003 |

* cited by examiner (A)

(B)

ABSORBENT ARTICLE AND SURFACE SHEET THEREOF

TECHNICAL FIELD

The present invention relates to an absorbent article using such a surface sheet that has a highly spatial appearance, has high cushioning effect, has a decreased contact area with the skin to avoid skin problem, and is excellent in shape retention of uneven emboss, and to the surface sheet.

BACKGROUND ART

As a surface material of an absorbent article, such a material has been conventionally placed into market that has an embossed pattern for various purposes, such as suppression of wet feeling by decreasing the touch area with skin, and improvement in touch feeling associated with improved texture. Examples of the material include those disclosed in Patent Documents 1 to 5 below.

Patent Document 1 discloses an absorbent article using a surface sheet having a large number of ridges and grooves disposed alternately to avoid a flat area, in which the ridges are curved convexly, the grooves are curved concavely, and the grooves have a large number of openings disposed with intervals.

Patent Document 2 discloses a surface sheet having plural first ribs and plural second ribs, in which the first ribs are each formed with a top and both side walls continuing from both sides of the top and curving toward the backside of the surface sheet, have a cross section having a downward U shape, and extend lengthwise with being spaced respectively, the second ribs each have a top and are formed with being spaced respectively between the side walls of the first ribs, openings are formed with the first ribs and second ribs, and the tops of the second ribs have a lower height than the tops of the first ribs.

Patent Document 3 discloses such an absorbent article in that a large number of fusion lines containing a large number of fusion points dented from the surface sheet are formed, the fusion lines extend obliquely with respect to the lengthwise direction of the absorbent article to form concave grooves in a lattice pattern, and the plural fusion points are present at intersecting points of the fusion lines to form lattice points.

Patent Document 4 discloses a plastic sheet having a thermal plasticity and having a melt pattern (emboss pattern) applied to the sheet surface, in which the melt pattern is formed in such a manner that, in the condition where the plastic sheet is stretched, a virtual line connecting areas having no melt pattern in the substantially stretching direction is not linearly continued but is formed in a zigzag form or a rhombic pattern form, so as to form convex-concave shaped wrinkles corresponding to the arrangement of the melt pattern.

Patent Document 5 discloses an absorbent article using such a surface sheet that has a large number of elevated portions discontinuous in the lengthwise direction and the widthwise direction of the sheet, has a sheet thickness of from 0.5 to 10 mm under a pressure of 0.5 $cN/cm^2$, and has a minimum distance between the adjacent elevated portions of from 0.5 to 15 mm, which is obtained in such a manner that after laminating fiber assemblies constituting first and second fiber layers, an emboss surface having a large number of pins disposed regularly (such as a peripheral surface of an emboss roll) is pressed onto the side of the first fiber layer to fuse the constitutional fibers of the first fiber layer and the second fiber layer at the positions pressed by the pins under heat.

Patent Document 1: JP-A-8-302555
Patent Document 2: JP-U-A-10-112
Patent Document 3: JP-A-7-328060
Patent Document 4: JP-A-2002-160293
Patent Document 5: JP-A-2003-126147

DISCLOSURE OF THE INVENTION

Problems to be Solved by the Invention

In the case of the surface sheet disclosed in Patent Document 1, however, a spatial appearance is exhibited on the sheet surface with the ridges and grooves disposed alternately, but the ridges are in contact with the skin in the form of lines to provide a large contact area with the skin, whereby skin trouble, such as abrasion, eczema and itch, cannot be effectively prevented, and sticky feeling of menstrual blood discharge cannot be avoided. Furthermore, there is such a problem in that a nonwoven fabric is insufficient in shape retention property of the ridges and grooves, and the degree of unevenness of the wavy shape is gradually decreased when the state where the sheet receives pressure is continued upon sitting and lying down.

In the case of the surface sheet disclosed in Patent Document 2, the first ribs are in contact with the skin in the form of lines to provide a large contact area with the skin, whereby skin trouble, such as abrasion, eczema and itch, cannot be effectively prevented, and sticky feeling of menstrual blood discharge cannot be avoided. Furthermore, the sheet structure containing the first ribs and the second ribs constitutes a peculiar configuration to complicate the production process, and thus it has not yet been put into practical use.

In the case of the absorbent article disclosed in Patent Document 3, emboss having a functionally particular shape is merely applied to the surface sheet, and a highly spatial appearance and a soft texture cannot be obtained.

In the case of the plastic sheet disclosed in Patent Document 4, although unpleasant appearance and feeling derived from a flat plastic sheet surface can be avoided, it has a texture formed with random wrinkles formed over the entire sheet surface, with an appearance of a fabric like a handkerchief before ironing, thereby providing a poor spatial appearance.

The surface sheet disclosed in Patent Document 5 can minimize the contact area with the skin and is excellent in cushioning effect since a large number of ridges protrude toward the skin. However, the fibers in the dent portions are thermally fused to a high density by pressing through the embossing treatment on the surface side, and thus blood and the like discharged are absorbed by the dent portions through capillary phenomenon to prevent from penetrating to the side of the absorbent. Accordingly, in the case, for example, where the amount of menstrual blood is large, sticky feeling occurs due to menstrual blood retained by the surface sheet. The fibers of the ridges can maintain the elevated amount thereof in a dry state, but there is a problem in insufficient retention of the unevenness, i.e., the elevated amount is decreased in a wet state through spontaneous compression of the fibers (contracted state) to decrease cushioning effect significantly.

Accordingly, a problem of the invention is to provide such an absorbent article that has a highly spatial appearance, has high cushioning effect, has a minimized contact area with the skin, prevents effectively skin problems, such as abrasion, eczema and itch, is improved in feeling to the skin, avoids sticky feeling upon absorption of a body fluid, and is improved in shape retention of uneven emboss to maintain continuously the uneven shape not only in a dry state but also upon absorption of a body fluid, and also is to provide a surface sheet thereof.

Means for Solving the Problems

In order to solve the problem, the invention relating to claim 1 provides an absorbent article containing an absorbent member intervening between a liquid-permeable surface sheet and a backside sheet, characterized in that the surface sheet is a multilayer sheet containing at least a nonwoven fabric layer constituting a skin contact surface layer and a plastic film layer that is laminated on the skin noncontact surface side remote from the nonwoven fabric layer, the plastic film layer containing a material having a melting point that is lower than that of the nonwoven fabric layer, and the surface sheet has been embossed to an uneven shape containing a large number of elevated portions protruding outward under heating condition that is not lower than a melting point of the plastic film layer and is lower than a melting point of the nonwoven fabric layer, and has been subjected to formation of a large number of openings.

In the invention relating to claim 1, the surface sheet is constituted by a multilayer sheet containing at least a nonwoven fabric layer constituting a skin contact surface layer and a plastic film layer that is laminated on the skin noncontact surface side remote from the nonwoven fabric layer, and the plastic film layer contains a material having a melting point that is lower than that of the nonwoven fabric layer. The surface sheet has been embossed to an uneven shape containing a large number of elevated portions protruding outward under heating condition that is not lower than a melting point of the plastic film layer and is lower than a melting point of the nonwoven fabric layer, and has been subjected to formation of a large number of openings.

Accordingly, the emboss formed on the surface sheet has an uneven shape containing a large number of elevated portions protruding outward, whereby the contact area to the skin is minimized to prevent effectively skin problems, such as abrasion, eczema and itch, the feeling to the skin is improved, and sticky feeling upon absorption of a body fluid can be avoided.

The embossing process is carried out under heating condition that is not lower than the melting point of the plastic film layer and is lower than the melting point of the nonwoven fabric layer, whereby the plastic film layer is deformed in a semimolten state or a molten state under heating to retain firmly the uneven curved shape obtained by the embossing process, and thus not only the cushioning effect is retained in a dry state but also the uneven shape is retained in a wet state. The nonwoven fabric layer constituting the surface layer undergoes less influence of heat upon embossing, and thus the texture can be retained.

As the invention relating to claim 2, the absorbent article according to claim 1 is provided, wherein the surface sheet is a multilayer sheet having two layers of a nonwoven fabric layer constituting a skin contact surface layer and a plastic film layer that is laminated on the skin noncontact surface side of the nonwoven fabric layer.

In the invention relating to claim 2, the surface sheet has a basic structure that is specifically a multilayer sheet having two layers of a nonwoven fabric layer constituting a skin contact surface layer and a plastic film layer that is laminated on the skin noncontact surface side of the nonwoven fabric layer.

As the invention relating to claim 3, the absorbent article according to claim 1 is provided, wherein the surface sheet is a multilayer sheet having three layers of a nonwoven fabric layer constituting a skin contact surface layer, a plastic film layer that is laminated on the skin noncontact surface side of the nonwoven fabric layer, and a nonwoven fabric layer that is laminated on the skin noncontact surface side of the plastic film layer.

In the invention relating to claim 3, the surface sheet has a basic structure that is specifically a multilayer sheet having three layers of a nonwoven fabric layer constituting a skin contact surface layer, a plastic film layer that is laminated on the skin noncontact surface side of the nonwoven fabric layer, and a nonwoven fabric layer that is laminated on the skin noncontact surface side of the plastic film layer.

As the invention relating to claim 4, the absorbent article according to one of claims 1 to 3 is provided, wherein the nonwoven fabric layer contains polypropylene, and the plastic film layer contains polyethylene.

In the invention relating to claim 4, the surface sheet is specifically constituted by the nonwoven fabric layer containing polypropylene and the plastic film layer containing polyethylene. The polypropylene has a melting point of 165° C., and the polyethylene has a melting point of 115° C. for low density and 137° C. for high density.

As the invention relating to claim 5, the absorbent article according to one of claims 1 to 4 is provided, wherein the embossing process to an uneven shape is carried out by applying interdigitation of a convex emboss roll having a large number of convex portions disposed thereon and a concave emboss roll having a large number of concave portions disposed thereon corresponding to the convex portions.

In the invention relating to claim 5, the embossing process to an uneven shape is carried out by applying interdigitation of a convex emboss roll having a large number of convex portions disposed thereon and a concave emboss roll having a large number of concave portions disposed thereon corresponding to the convex portions. By applying emboss through interdigitation of the convex portions and the concave portions, the surface sheet undergoes no extreme difference in fiber density between the region having a high fiber density and the region having a low fiber density, whereby a body fluid is not retained with the region having a high fiber density to avoid sticky feeling upon absorption of a body fluid.

As the invention relating to claim 6, the absorbent article according to claim 5 is provided, wherein the convex emboss roll and the concave emboss roll have a depth of the concave portions that is larger than a height of the convex portions.

In the invention relating to claim 6, the convex emboss roll and the concave emboss roll have a depth of the concave portions that is larger than a height of the convex portions. Accordingly, the emboss is applied while avoiding such a portion in that the convex emboss roll and the concave emboss roll are not in contact with each other, whereby the embossing can be effected without formation of a region having a high fiber density in the nonwoven fabric layer of the surface sheet.

As the invention relating to claim 7, the absorbent article according to one of claims 1 to 6 is provided, wherein a distance among concave portions of the uneven emboss formed on the surface sheet is from 3 to 7 mm.

In the invention relating to claim 7, the distance among the concave portions of the uneven emboss formed on the surface sheet is from 3 to 7 mm. As shown in examples described later, in the case where the elevated portions are disposed to provide a distance among the concave portions of from 3 to 7 mm, whereby a high spatial appearance and high cushioning effect are provided. As a result, the feeling to the skin is improved, and sticky feeling upon absorption of a body fluid can be avoided.

As the invention relating to claim 8, the absorbent article according to one of claims 1 to 7 is provided, wherein the large number of openings are formed at least in an area containing the concave portions in the surface sheet.

In the invention relating to claim 8, the large number of openings are formed at least in an area containing the concave portions in the surface sheet, whereby a body fluid having flowed into the concave portions along the elevated portions of the surface sheet can be quickly absorbed with the absorbent member without accumulation.

As the invention relating to claim 9, the absorbent article according to one of claims 1 to 8 is provided, wherein a second sheet containing a hydrophilic fiber layer is laminated on the skin noncontact surface side of the surface sheet, and the second sheet is embossed along with the surface sheet.

In the invention relating to claim 9 where a hydrophilic second sheet as a separate member is laminated on the surface sheet, a space is formed between the second sheet and the surface sheet (particularly at the convex portions of the emboss). Thus, the second sheet is embossed along with the surface sheet, whereby a body fluid present on the surface sheet is quickly absorbed with the second sheet, and the body fluid can be prevented from remaining on the surface. Furthermore, high cushioning effect can be obtained with the second sheet.

As the invention relating to claim 10, the absorbent article according to claim 9 is provided, wherein the second sheet is an air-through nonwoven fabric.

In the invention relating to claim 10, an air-through nonwoven fabric is used as the second sheet. High cushioning effect can be imparted to the surface sheet by the bulky property of the air-through nonwoven fabric.

The invention relating to claim 11 provides a surface sheet containing a multilayer sheet containing at least a nonwoven fabric layer constituting a skin contact surface layer and a plastic film layer that is laminated on the skin noncontact surface side remote from the nonwoven fabric layer, the plastic film layer containing a material having a melting point that is lower than that of the nonwoven fabric layer, and the surface sheet having been embossed to an uneven shape containing a large number of elevated portions protruding outward under heating condition that is not lower than a melting point of the plastic film layer and is lower than a melting point of the nonwoven fabric layer, and has been subjected to formation of a large number of openings.

Advantages of the Invention

According to the invention having been described in detail, the absorbent article has a highly spatial appearance, has high cushioning effect, has a minimized contact area with the skin, prevents effectively skin problems, such as abrasion, eczema and itch, is improved in feeling to the skin, and avoids sticky feeling upon absorption of a body fluid. Furthermore, the plastic film layer is deformed in a semimolten state or a molten state, whereby the shape retention property of the uneven emboss can be improved while maintaining the texture of the surface nonwoven fabric layer, and thus the uneven shape can be retained not only in a dry state but also upon absorbing a body fluid.

BEST MODE FOR CARRYING OUT THE INVENTION

Embodiments of the invention will be described in detail with reference to the drawings. FIG. 1 is a partially cutaway perspective view of a thin sanitary napkin 1 according to the invention.

(Structure of Absorbent Article 1)

The sanitary napkin 1 is subjected mainly to such purposes as a panty liner, a sanitary napkin, a vaginal discharge absorbent sheet and an incontinence pad, and as shown in FIG. 1, for example, has such a structure in that an absorbent member 4 or an absorbent member 4 having been surrounded with crape paper 5 intervenes between a liquid-impermeable backside sheet 2 and a liquid-permeable surface sheet 3 (which is hereinafter referred simply to as a surface sheet), and a hydrophilic second sheet 6 is disposed between the surface sheet 3 and the absorbent member 4. Around the absorbent member 4, the liquid-impermeable backside sheet 2 and the surface sheet 3 are bonded with an adhesion means, such as a hot-melt adhesive.

As the liquid-impermeable backside sheet 2, a sheet material having water intercepting property, such as polyethylene and polypropylene, is used, and a nonwoven fabric sheet that has been ensured to have liquid-impermeability through a waterproof film (the liquid-impermeable backside sheet is constituted by a waterproof film and a nonwoven fabric, in this case) may be also be used. In recent years, a material having moisture permeability is favorably used from the standpoint of prevention of getting stuffy. As the water intercepting and moisture-permeable sheet material, such a finely porous sheet is favorably used that is obtained by melting and kneading an inorganic filler in an olefin resin, such as polyethylene and polypropylene, to form a sheet, and then stretching the sheet uniaxially or biaxially.

The surface sheet 3 is a multilayer sheet having at least a nonwoven fabric layer constituting a skin contact surface layer and a plastic film layer that is laminated on the skin noncontact surface side remote from the nonwoven fabric layer, in which the surface sheet has been embossed to an uneven shape containing a large number of elevated portions 7, 7 . . . protruding outward, and has been subjected to formation of a large number of openings. The surface sheet 3 will be specifically described later.

The absorbent member 4 intervening between the liquid-impermeable backside sheet 2 and the surface sheet 3 is, for example, a member obtained by mixing a high water-absorbing resin in pulp, or a member obtained by mixing chemical fibers in pulp and further mixing a high water-absorbing resin therein. The absorbent member 4 is preferably surrounded with crape paper 5 for retaining the shape and diffusing menstrual blood and the like, and for preventing menstrual blood and the like from being refluxed. Examples of the pulp include those containing cellulose fibers, such as chemical pulp and fused pulp obtained form wood, and artificial cellulose fibers, such as rayon and acetate fibers. Softwood pulp having a long fiber length is preferably used as compared to hardwood pulp from the standpoint of function and cost.

Examples of the high water-absorbing resin include a polyacrylate salt crosslinked product, a self-crosslinked polyacrylate salt, a saponified product of an acrylate ester-vinyl acetate copolymer, a an isobutyrene-maleic anhydride copolymer crosslinked product, a polysulfonate salt crosslinked product, and a material obtained by partially crosslinking a water swelling polymer, such as polyethylene oxide and polyacrylamide. Among these, materials based on acrylic acid or an acrylate salt are preferred since they are excellent in water absorbing amount and water absorbing rate. The high water-absorbing resin having water absorbing capability can be controlled in water absorbing power and water absorbing rate by controlling the crosslinking density and the crosslinking density gradient in the production process. The content of the high water-absorbing resin is preferably from 10 to 60%. In the case where the content of the high water-absorbing resin is less than 10%, sufficient absorbing capability cannot be provided, and in the case where it exceeds 60%, entanglement among the pulp fibers is diminished to provide such a tendency that the sheet strength is lowered to cause tearing and breakage.

The hydrophilic second sheet 6 disposed between the liquid-permeable surface sheet 3 and the absorbent member 4 may have hydrophilicity to a body fluid. Specifically, a material having hydrophilicity by itself using regenerated fibers, such as rayon and cupra, or natural fibers, such as cotton, or fibers having been imparted with hydrophilicity by surface treatment of synthetic fibers, such as an olefin series, e.g., polyethylene and polypropylene, a polyester series and a polyamide series, with a hydrophilic agent can be used. The second sheet 6 is preferably bonded to the backside surface of the surface sheet 3 by hot-melt or fusion (emboss), and is preferably embossed along with the surface sheet 3 in a state where these sheets are laminated.

(Structure of Surface Sheet 3)

The surface sheet 3 is a liquid-permeable sheet containing a multilayer sheet having at least a nonwoven fabric layer constituting a skin contact surface layer and a plastic film layer that is laminated on the skin noncontact surface side remote from the nonwoven fabric layer, and the surface sheet has been embossed to an uneven shape containing a large number of elevated portions 7, 7 . . . protruding outward, and has been subjected to formation of a large number of openings.

The substrate structure of the surface sheet 3 may be a sheet having a two-layer structure containing hydrophobic nonwoven fabric layer 3A/plastic film layer 3B as shown in FIG. 2(A), a sheet substrate having a three-layer structure containing hydrophobic nonwoven fabric layer 3A/plastic film layer 3B/hydrophobic nonwoven fabric layer 3C as shown in FIG. 2(B), or a sheet substrate having a three-layer structure containing hydrophobic nonwoven fabric layer 3A/plastic film layer 3B/hydrophilic nonwoven fabric layer 3C.

The fiber material constituting the nonwoven fabric layers 3A and 3C may be synthetic fibers, such as an olefin series, e.g., polyethylene and polypropylene, a polyester series and a polyamide series, and may also be regenerated fibers, such as rayon and cupra, or natural fibers, such as cotton, and nonwoven fabrics obtained by an appropriate process, such as an air-through method, a spun lace method, a spunbond method, a thermal bond method, a melt blown method and a needle punch method, may be used. Among these methods, a spun lace method is favorable since rich drape is provided, and an air-through method and a thermal bond method are favorable since bulkiness and softness are provided. The fibers of the nonwoven fabric may be either continuous fibers or discontinuous fibers, and discontinuous fibers are preferably used for providing texture of towel cloth. A nonwoven fabric containing olefin fibers, such as polyethylene or polypropylene, having a relatively low melting point is preferably used for facilitating the embossing process. Core-shell fibers containing fibers having a high melting point as a core and fibers having a low melting point as a shell, and composite fibers, such as side-by-side fibers and split fibers, may also preferably used.

The material of the plastic sheet 3B may be preferably an olefin resin, such as polyethylene and polypropylene, a polyamide resin, such as polyester and nylon, and an ethylene-vinyl acetate copolymer (EVA).

In the surface sheet 3, the materials are appropriately selected from the group of materials for the nonwoven fabric and the group of materials for the plastic film in such a manner that the material of the plastic film layer 3B has a melting point that is relatively lower than that of the nonwoven fabric layers 3A and 3C. In the embossing process, the surface sheet is embossed to an uneven shape containing a large number of elevated portions 7, 7 . . . protruding outward under heating condition that is not lower than the melting point of the plastic film layer 3B and is lower than the melting point of the nonwoven fabric layers 3A and 3C, and is subjected to formation of a large number of openings (not shown in the figure).

One of the most common examples of the combination of materials is such a combination in that the material of the nonwoven fabric layers 3A and 3C is polypropylene, and the material of the plastic film layer 3B is polyethylene. Since the polypropylene has a melting point of 165° C., and the polyethylene has a melting point of 115° C. for low density and 137° C. for high density, the heating temperature of rolls in the embossing process is set at a temperature exceeding 115° C. (137° C.) and less than 165° C., whereby only the plastic film layer 3B is deformed in a semimolten state or a molten state. After the embossing process, accordingly, the uneven curved shape can be firmly retained, and thus not only the cushioning effect is retained in a dry state but also the uneven shape is retained in a wet state. In the case where a heating temperature exceeding the melting point of the nonwoven fabric layers 3A and 3B is used, the entire surface of the nonwoven fabric layer 3A constituting the surface layer is plasticized and hardened, whereby the texture and feeling to the skin on the surface are damaged.

Upon subjecting the surface sheet 3 to the embossing process, a convex emboss roll 10 having a large number of convex portions 10a, 10a . . . disposed thereon as shown in FIG. 4 and a concave emboss roll 11 having a large number of concave portions 11a, 11a . . . disposed thereon corresponding to the convex portions 10a, 10a . . . as shown in FIG. 5 are used, and the surface sheet 3 is passed between the convex emboss roll 10 and the concave emboss roll 11 to apply emboss through interdigitation of the convex portions 10a and the concave portions 11a.

In this case, the height h1 of the convex portions 10a of the convex emboss roll 10 is preferably about from 1.5 to 2.5 mm, and the depth h2 of the concave portions 11a of the concave emboss roll 11 is preferably about from 1.7 to 2.7 mm. It is also preferred that the depth of the concave portions 11a is made larger than the height of the convex portions 10a, whereby in the interdigitated state as shown in FIG. 6, the convex portions 10a are not in contact with the concave portions 11a to provide overall a prescribed gap, specifically from 0.1 to 0.5 mm, and preferably from 0.2 to 0.4 mm. By applying emboss with avoiding such a portion in that the concave portions 11a and the convex portions 10a are in contact with each other, emboss can be applied without formation of a high density region of the fibers in the nonwoven fabric layer 3A of the surface sheet 3.

The distance P among concave portions of the uneven emboss formed on the surface sheet 3 is desirably from 3 to 7 mm, and preferably from 3 to 6 mm. In the case where the distance P among concave portions is less than 3 mm, the elevated portions 7 and 7 are too close to each other to make the special appearance poor and to fail to obtain target cushioning effect. In the case where the distance P among concave portions exceeds 7 mm, the distance is too large to fail to obtain target cushioning effect. Furthermore, the concave portions are in contact with the skin to provide poor feeling to the skin and to fail to avoid sticky feeling upon absorbing a body fluid.

The areal weights of the nonwoven fabric layer 3A in contact with the skin, the intermediate plastic film layer 3B and the nonwoven fabric layer 3C as a lower layer are preferably from 10 to 20 g/m², from 5 to 15 g/m² and from 10 to 20 g/m², respectively. It is preferred in this case that the areal weight of the nonwoven fabric layer 3A as an upper layer is as relatively smaller as from 10 to 15 g/m² for preventing sticky feeling.

The openings formed in the surface sheet 3 may have an opening area per one opening of from 0.35 to 0.60 mm², and preferably from 0.47 to 0.54 mm² with an opening ratio of from 10 to 19%, and preferably from 11 to 14%. In the case where the opening area is less than 0.35 mm², the opening area is too small, and thus a body fluid is accumulated on the wall of the openings. In the case where the opening area exceeds 0.60 mm², it is not preferred since reflux of a body fluid occurs through the openings. In the case where the opening ratio is less than 10%, the opening ratio is too small, and thus a body fluid discharged on the surface cannot be transmitted quickly. In the case where it exceeds 19%, it is not preferred since reflux of a body fluid occurs.

The openings are preferably formed only in the concave portions except for the elevated portions 7 and 7, or formed in regions surrounding the concave portions. By forming the openings in at least regions including the concave portions, a body fluid flowing into the concave portions along the elevated portions 7 and 7 of the surface sheet 3 can be quickly absorbed with the absorbent member 4.

In order to form the opening, such methods may be employed as a method, in which the plastic film layer 3B is softened near the softening temperature and placed on a support having a large number of openings, and the film is sucked under the support or pressurized above the support with air pressure to form the openings, and a method, in which the film is impaled with heated needles. The opening formation process may be carried out after laminating the nonwoven fabric layer 3A (3C) and the plastic film layer 3B to form openings in all the layers laminated, but it is sufficient that at least the plastic film layer 3B is subjected thereto. In the opening formation process in this case, openings are formed in the plastic film layer 3B, which is then laminated on the nonwoven fabric layer 3A (3B).

EXAMPLES (1) Cushioning Effect Test with Difference in Distance P Among Concave Side In this example, variation in cushioning effect with difference in distance P among the concave portions was investigated. In the test, specimens were produced with a convex emboss roll 10 having a height h1 of the convex portions 10a fixed to 1.8 mm and a concave emboss roll 11 having a depth h2 of the concave portions 11a fixed to 1.8 mm and a distance P among the concave portions varying in a range of from 2.5 to 10 mm, and these specimens and a specimen subjected to no embossing process were tested for WC value (compression energy) with a KES Compression Tester as an index of cushioning effect.

The KES Compression Tester (produced by Kato Tech Co., Ltd.) is a tester for simulating feeling obtained upon touching an article with a human finger, and can measure compression energy, compression hardness, compression restoration and the like. In the measurement, a specimen is compressed at a speed of 0.1 cm/sec, a compression area of 2 cm², SENS of 2 (load 200 g/10 v), DEF sensitivity of 5 and a compression load of 50 gf/cm², as shown in FIG. 7(A), and LC (compression hardness), WC (compression energy) and RC (compression restoration) are calculated from the correlation chart of the pressure and the deformation amount.

In the correlation chart of the pressure and the deformation amount shown in FIG. 7(B), the LC (compression hardness) is expressed by (area of a+b)/(area of $\triangle ABC$) and is evaluated as having higher compression hardness when the value is close to 1. The WC (compression energy) is expressed by (area of a+b) and is evaluated as being easily compressed when the value is larger. The RC (compression restoration) is expressed by (area of b)/(area of a+b) and is evaluated as having larger restoration property when the value is close to 100%. Among these test items, it is said that the WC (compression energy) is preferred as an index of softness (cushioning effect) determined by sensory evaluation.

The test results are shown in Table 1 below and in FIG. 8.

TABLE 1

| Distance P among Concave Portions (mm) | Compression Work Amount (gf · cm/cm²) | Thickness (mm) |
| --- | --- | --- |
| 2.5 | 1.32 | 2.10 |
| 5.0 | 1.43 | 2.22 |
| 7.5 | 1.15 | 1.99 |
| 10.0 | 0.97 | 1.91 |
| blank (no process) | 0.98 | 1.68 |

In the graph with the distance amount concave portions as the abscissa and the compression work amount as the ordinate as shown in FIG. 8, an upward convex curve is obtained totally, and it is found that particularly high cushioning effect is obtained when the distance amount P the concave portions is set in a range of from 3 to 7 mm.

Figure 1:
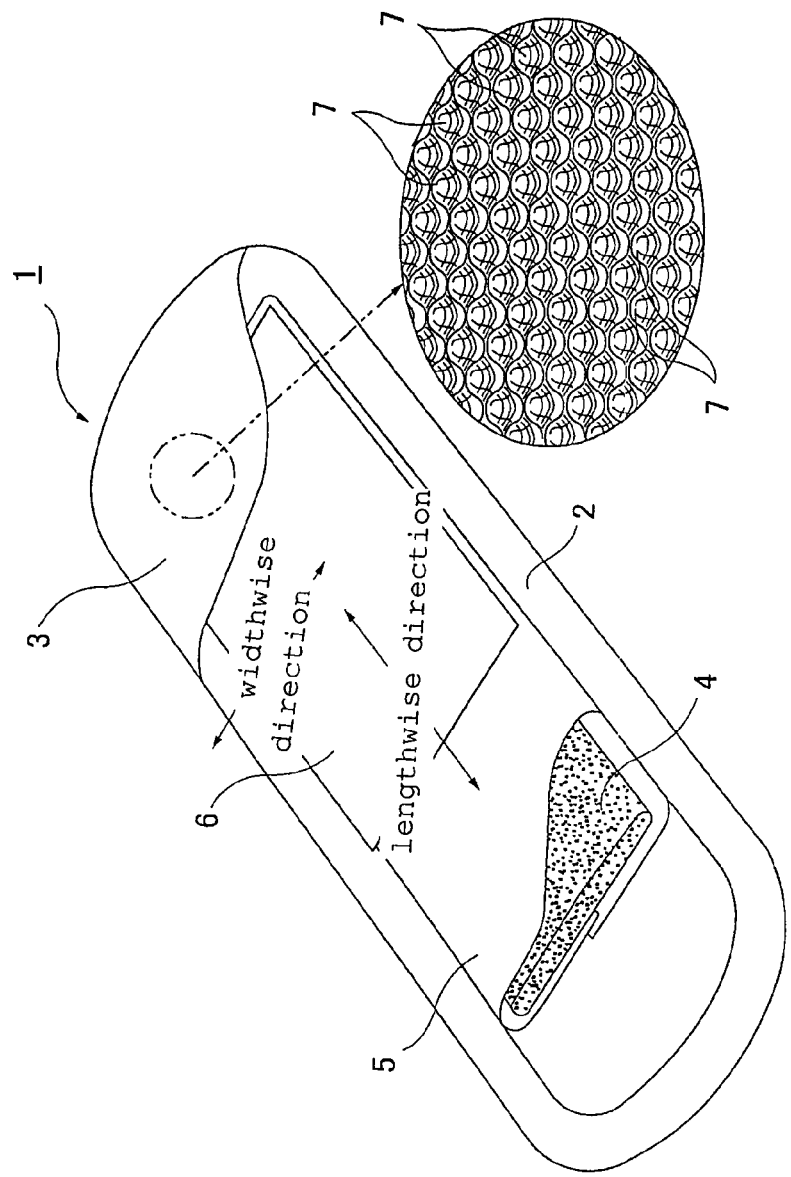
[FIG. 1] It is a partially cutaway perspective view of an absorbent article 1 according to the invention.
Figure 2:
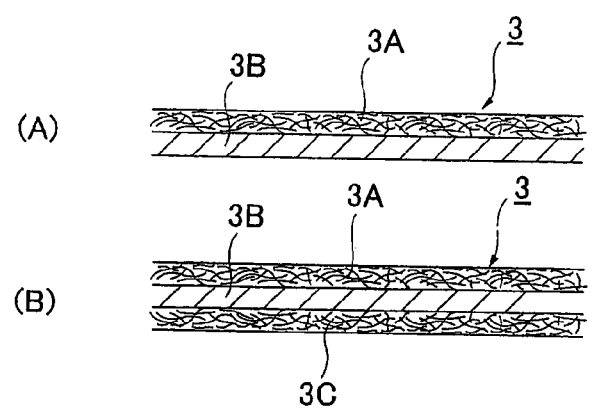
[FIG. 2] It is a diagram showing a cross sectional constitution of a liquid-permeable surface sheet 3 (before emboss process)
Figure 3:
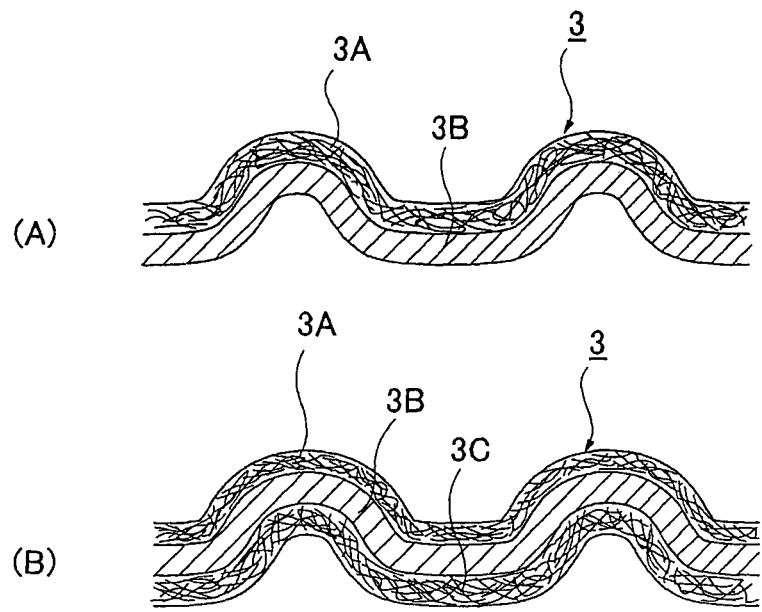
[FIG. 3] It is a diagram showing a cross sectional constitution of a liquid-permeable surface sheet 3 (after emboss process).
Figure 4:
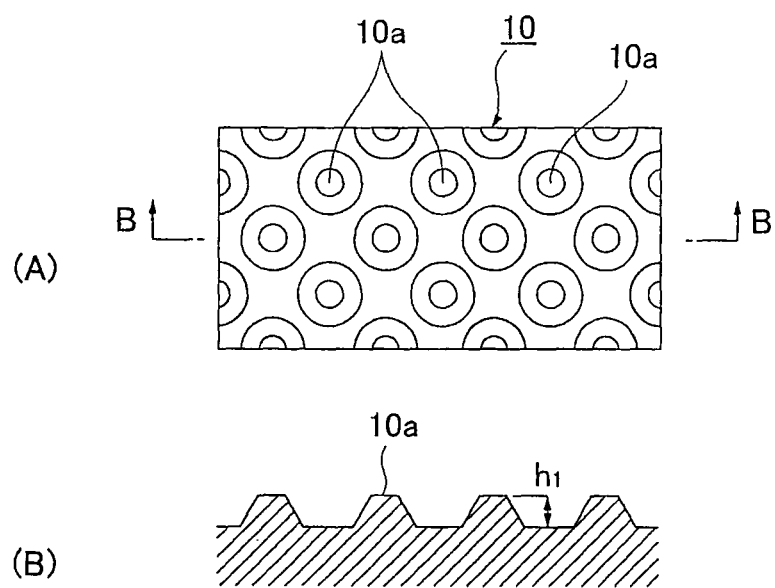
[FIG. 4] It shows a convex emboss roll 10, in which (A) is a plane view, and (B) is a view along line B-B thereof.
Figure 5:
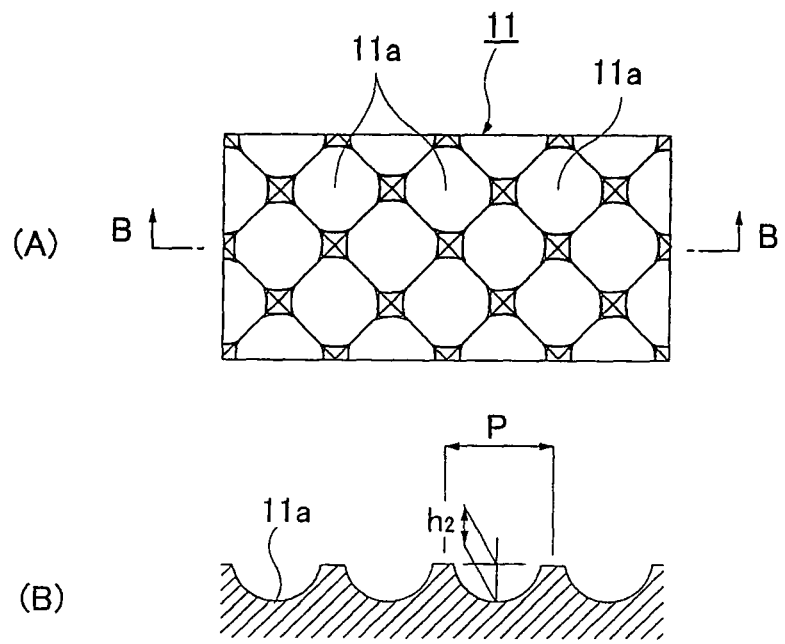
[FIG. 5] It shows a concave emboss roll 11, in which (A) is a plane view, and (B) is a view along line B-B thereof.
Figure 6:
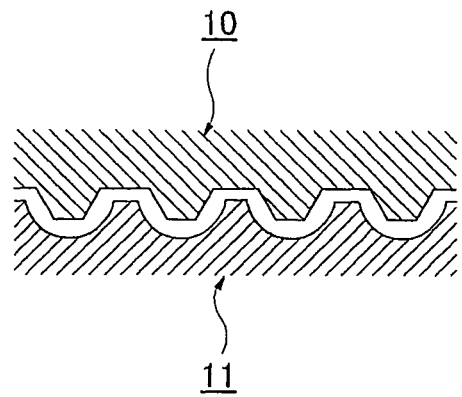
[FIG. 6] It is a diagram showing an interdigitation state of a convex emboss roll 10 and a concave emboss roll 11.
Figure 7:
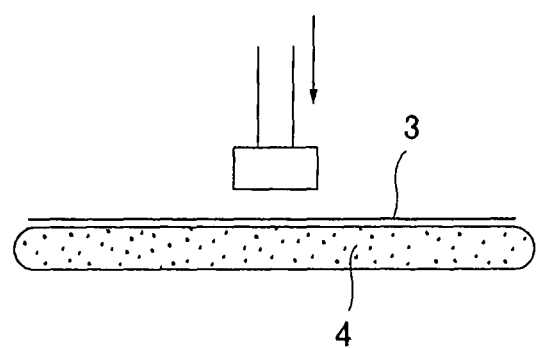
[FIG. 7] (A) is a diagram showing summary of a test with KES Compression Tester, and (B) is a correlation chart of pressure and deformation amount showing results of the KES compression test.
Figure 7:
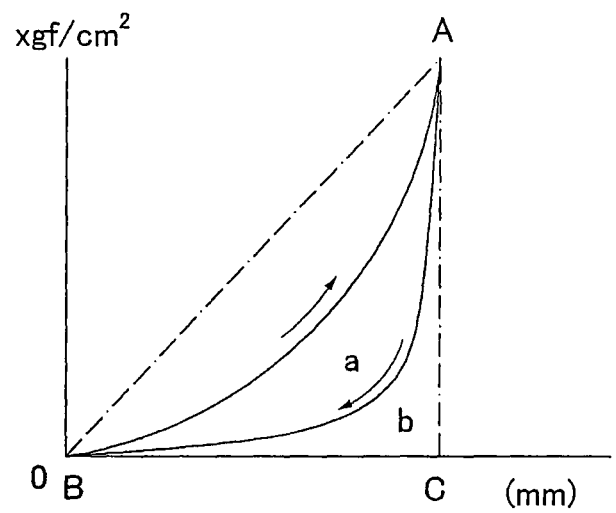
Figure 8:
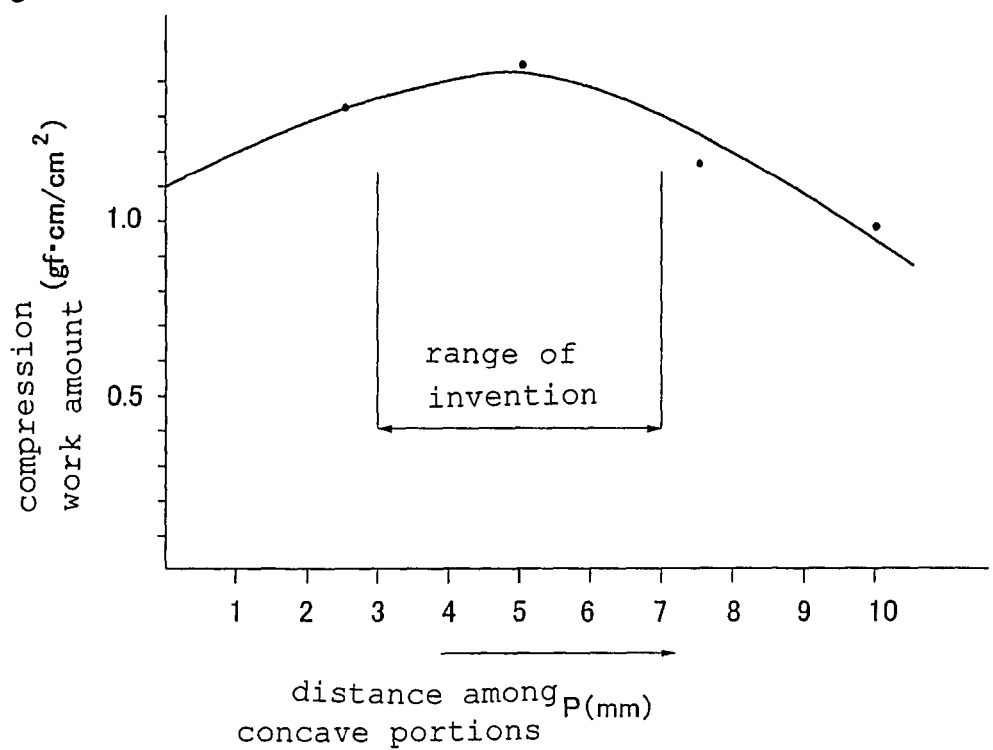
[FIG. 8] It is a graph showing test results of Example.

| DESCRIPTION OF SYMBOLS | |
| --- | --- |
| 1 | absorbent article (sanitary napkin) |
| 2 | liquid-impermeable backside sheet |
| 3 | liquid-permeable surface sheet |
| 4 | absorbent member |
| 5 | crape paper |
| 6 | second sheet |
| 7 | elevated portion |
| 10 | convex emboss roll |
| 10a | convex portions |

-continued

| DESCRIPTION OF SYMBOLS | |
|---|---|
| 11 | concave emboss roll |
| 11a | concave portions |

The invention claimed is:

1. An absorbent article comprising an absorbent member interposed between a liquid-permeable multilayer surface sheet and a backside sheet, the multilayer surface sheet comprising a nonwoven fabric layer having a skin contact surface side and a non-skin contact surface side and a plastic film layer laminated on the non-skin contact surface side of the nonwoven fabric layer, the plastic film layer comprising a material having a melting point that is lower than a melting point of the nonwoven fabric layer, the multilayer surface sheet being provided with an uneven surface contour including a plurality of elevated portions protruding outward, the uneven surface contour being formed by embossing the multilayer surface sheet with heating to a temperature that is not lower than a melting point of the plastic film layer and that is lower than a melting point of the nonwoven fabric layer, whereby only the plastic film layer is deformed by the embossing and heating, the uneven surface contour of the multilayer surface sheet being retained after the heating and embossing, the multilayer surface sheet having a plurality of through holes.

2. The absorbent article according to claim 1, wherein the multilayer surface sheet has two layers, the first of the two layers being the nonwoven fabric layer and the second of the two layers being the plastic film layer laminated on the non-skin contact surface side of the nonwoven fabric layer.

3. The absorbent article according to one of claim 1 or 2, wherein the nonwoven fabric layer comprises polypropylene, and the plastic film layer comprises polyethylene.

4. The absorbent article according to claim 1, wherein the surface sheet is a multilayer sheet having three layers, the three layers comprising, as a first nonwoven fabric layer, the nonwoven fabric layer having the skin contact surface side and the non-skin contact surface side, the plastic film layer laminated on the non-skin contact surface side of the first nonwoven fabric layer, and a second nonwoven fabric layer laminated on the plastic film layer, wherein the plastic film layer is intermediate the first and second nonwoven fabric layers.

5. The absorbent article according to claim 4, wherein each of the first and second nonwoven fabric layers comprise polypropylene, and the plastic film layer comprises polyethylene.

6. The absorbent article according to claim 1, wherein the multilayer surface sheet is embossed to an uneven surface contour through an embossing process in which the multilayer surface sheet is subjected to heat and pressure simultaneously applied by a convex emboss roll having on a surface thereof a plurality of convex portions and a concave emboss roll having on a surface thereof a plurality of concave portions, wherein the convex portions and concave portions cooperate in an interdigitated relationship when pressure is simultaneously applied to the multilayer surface sheet by the convex and concave emboss rolls to form the elevated portions protruding outward from the multilayer surface sheet.

7. The absorbent article according to claim 6, wherein the concave portions have a depth dimension that is larger than a height dimension of the convex portions.

8. The absorbent article according to claim 6, wherein the concave portions are distanced 3 to 7 mm apart from each other on the concave emboss roll.

9. The absorbent article of claim 6, wherein the plurality of convex portions cover the surface of the convex emboss roll and the plurality of concave portions cover the surface of the concave emboss roll.

10. The absorbent article according to claim 1, wherein the plurality of through holes are formed at least in the elevated portions in the multilayer surface sheet.

11. The absorbent article according to claim 1, wherein a hydrophilic fiber layer is laminated on a back side of the multilayer surface sheet, and the hydrophilic fiber layer is embossed with the multilayer surface sheet.

12. The absorbent article according to claim 11, wherein the hydrophilic fiber layer is an air-permeable nonwoven fabric.

13. The absorbent article of claim 1, wherein the plurality of elevated portions cover the surface of the multilayer sheet.

14. The absorbent article according to claim 13, wherein the plurality of through holes are formed in the elevated portions that cover the surface of the multilayer surface sheet.

15. The absorbent article of claim 1, wherein the plurality of through holes are provided over the surface of the multilayer sheet.

16. A multilayer surface sheet comprising a nonwoven fabric layer having a skin contact surface side and a non-skin contact surface side and a plastic film layer laminated on the non-skin contact surface side of the nonwoven fabric layer, the plastic film layer comprising a material having a melting point that is lower than a melting point of the nonwoven fabric layer, the surface sheet being provided with an uneven surface contour including a plurality of elevated portions protruding outward that are formed by embossing the multilayer surface sheet with heating to a temperature that is not lower than a melting point of the plastic film layer and that is lower than a melting point of the nonwoven fabric layer, whereby only the plastic film layer is deformed by the embossing and heating, the uneven surface contour of the multilayer surface sheet being retained after the heating and embossing, the multilayer surface sheet having a plurality of through holes.

17. The absorbent article of claim 16, wherein the plurality of elevated portions cover the surface of the multilayer sheet.

18. The absorbent article of claim 16, wherein the plurality of through holes are provided over the surface of the multilayer sheet.

* * * * *